US010531978B2

(12) United States Patent
Haas et al.

(10) Patent No.: US 10,531,978 B2
(45) Date of Patent: Jan. 14, 2020

(54) SYSTEM FOR THE PRODUCTION OF A MEDICAL PRODUCT, AS WELL AS METHOD FOR OPERATION OF SUCH A SYSTEM

(71) Applicant: KIEFEL GmbH, Freilassing (DE)

(72) Inventors: Johann Haas, Koestendorf (AT); Juergen Baumann, Chieming (DE)

(73) Assignee: KIEFEL GmbH (DE)

( * ) Notice: Subject to any disclaimer, the term of this patent is extended or adjusted under 35 U.S.C. 154(b) by 486 days.

(21) Appl. No.: 14/789,186

(22) Filed: Jul. 1, 2015

(65) Prior Publication Data

US 2016/0000599 A1 Jan. 7, 2016

(30) Foreign Application Priority Data

Jul. 2, 2014 (DE) .......................... 10 2014 009 682

(51) Int. Cl.
*B31B 70/00* (2017.01)
*A61F 5/445* (2006.01)

(52) U.S. Cl.
CPC .............. *A61F 5/445* (2013.01); *B31B 70/00* (2017.08)

(58) Field of Classification Search
CPC ....... B31B 70/00; B31B 70/04; B31B 70/005; A61F 5/445
USPC .................................................. 493/205, 189
See application file for complete search history.

(56) References Cited

U.S. PATENT DOCUMENTS

| 4,388,135 A | 6/1983 | Jensen |
| 5,288,284 A | 2/1994 | Achelpohl et al. |
| 5,657,529 A * | 8/1997 | Bohn ...................... B41F 17/02 |
| | | 226/101 |
| 6,588,745 B2 | 7/2003 | Gosslinghof |
| 2006/0100080 A1* | 5/2006 | Totani ..................... B29C 65/02 |
| | | 493/147 |
| 2010/0192367 A1* | 8/2010 | Kishimoto ............. B31B 70/00 |
| | | 29/773 |

(Continued)

FOREIGN PATENT DOCUMENTS

| DE | 41 41 466 A1 | 6/1993 |
| EP | 0 045 587 A1 | 2/1982 |

(Continued)

OTHER PUBLICATIONS

European Search Report dated Nov. 17, 2015 in EP 15 00 1855, with English translation of relevant parts.
"Colostomy Bag Line", May 31, 2015 (May 31, 2015), XP-055226105.

*Primary Examiner* — Chelsea E Stinson
(74) *Attorney, Agent, or Firm* — Tarolli, Sundheim, Covell & Tummino LLP (57) ABSTRACT

A system for the production of a medical product, above all in the form of an ostomy bag, as well as a method for operation of such a system, uses a highly flexible modular system concept, in which individual feed lines for semi-finished products are provided. The feed lines can transfer semi-finished products to a main line in pre-assembled manner. In the main line, ultimate processing of the semi-finished products to produce the finished product or a further semi-finished product takes place, with the greatest possible work precision, in contrast to conventional systems that guide different film systems in different planes at a distance from one another, to allow pre-processing steps, before bringing the films together in one plane and welded to one another.

23 Claims, 7 Drawing Sheets

(56) References Cited

U.S. PATENT DOCUMENTS

2011/0028924 A1\* 2/2011 Murray ................ A61F 5/4407
                                                                                                  604/332

FOREIGN PATENT DOCUMENTS

| EP | 1 227 025 A1 | 7/2002 |
| FR | 2 164 294 A5 | 7/1973 |
| GB | 1 392 109 A | 4/1975 |

\* cited by examiner

SYSTEM FOR THE PRODUCTION OF A MEDICAL PRODUCT, AS WELL AS METHOD FOR OPERATION OF SUCH A SYSTEM

CROSS REFERENCE TO RELATED APPLICATIONS

Applicant claims priority under 35 U.S.C. § 119 of German Application No. 10 2014 009 682.3 filed Jul. 2, 2014, the disclosure of which is incorporated by reference.

BACKGROUND OF THE INVENTION

1. Field of the Invention

The invention relates to a system for the production of a medical product, as well as to a method for operation of such a system.

2. Description of the Related Art

For the production of bags for medical purposes, it is known to guide the required film plies in separate planes from one another, and to bring them into one plane to weld them, and to transport them further in this plane, in the welded state.

This practice holds true, above all, for a main area of use of the present invention here, namely for medical bags that have an opening in a top side or a bottom side, above all therefore for any kind of ostomy bags, above all colostomy bags.

SUMMARY OF THE INVENTION

The present invention is based on the task of providing support to the state of the art with an alternative or an improvement.

According to a first aspect of the invention, this task is accomplished by a system for the production of a medical product in the form of an ostomy bag, particularly a colostomy bag, composed of multiple plies of film and/or nonwoven, having a semi-finished product transport system, particularly a tray transport system, having a main line and multiple feed lines disposed laterally, wherein semi-finished product feed lines are provided, in order to feed pre-worked semi-finished products from the feed lines to the main line in automated manner, as well as having feed line tools on the feed lines, and having a main line tool on the main line.

With regard to terminology, the following explanation is provided:

First of all, it is explicitly pointed out that within the scope of the present patent application here, indefinite articles and numerical information such as "one," "two," etc. should be understood, in general, as minimum information, in other words as "at least one . . . ," "at least two . . . ," etc., unless something different is explicitly or implicitly evident from the respective contexts, or it is evident to a person skilled in the art that it is technically compulsory that only "precisely one . . . ," "precisely two . . . ," etc. can be meant or should be meant there.

Furthermore, it should be pointed out that whenever a control unit or regulation unit is mentioned, both terms are intended to be disclosed, in each instance, wherein a "control unit" should be understood to mean a general term for a "regulation unit."

The system presented here produces an ostomy bag. The bag itself is markedly two-dimensional in the freshly produced, flat state, in other words provided with a top side and a bottom side. On at least one of the two sides, in other words on the top side and/or bottom side, an inlet and/or outlet is provided on an ostomy bag.

A "film" should be understood to be a markedly two-dimensional structure composed of plastic, particularly a thermoplastic. Possible variants are not only a nonwoven, but also, for example, a knitted fabric, a laid scrim, a woven fabric, a loom-knitted fabric, or a nonwoven fabric. The semi-finished products, however, should be present in "plies."

The plies can be transported to the system as finished sections, for example, or, alternatively, an unwinding station is provided, for example, onto which a roller can be hung, so that the system can pull off the individual pieces of the plies, which are required as sections, from the roller and cut them to size.

The plies are supposed to be present in the system, sooner or later, as "sections" of a discrete nature, thereby as individual panels, wherein a panel preferably comprises only one ostomy bag or other bag.

The "semi-finished product transport system" is supposed to be set up for transporting the semi-finished products along the feed lines and along the main line, based on a section of a ply, in each instance. Transporting particularly includes feed to tool stations and further guidance beyond the tool stations.

In a "tray transport system" individual, discrete trays are provided, which transport the sections or the semi-finished products produced from them. The trays themselves can be transported through the system by means of a belt drive, a magnetic drive, an entrainment drive or any desired other drive, for example.

The machine direction of such a system is fanned out, namely from the feed lines to a main line, and in the main line from a first feed line to the discharge point from the system, ideally with the finished product.

The semi-finished product transport system preferably has discrete transport means for one section of the plies, in each instance.

The "semi-finished product feed unit" is supposed to be set up for taking over the pre-worked semi-finished products when they come from the feed lines, in fully automated manner, and to transfer them from a feed line to the main line, in each instance.

Feed line tools are supposed to be provided on the feed lines, in other words at least two feed lines are supposed to be provided, which each have at least one tool.

The main line is supposed to have at least one main tool.

It is advantageous if the first aspect of the invention achieves very great variability in the production of the ostomy bags: By means of the semi-finished product feed units, which each serve as a transfer device between a feed line and the main line, it is possible to interchange one or more, sometimes even all the feed lines, for example if a product change is to be carried out. Parts of the system can nevertheless remain. If the feed lines are disposed with a sufficient distance from one another laterally, the feed lines can be easily displaced sideways, for example, in other words parallel to the main line, in other words between a rest position and a working position in which they are connected with the main line. In such a constellation, a product change can therefore be carried out without any loss of space.

According to a second aspect of the present invention, the stated task is accomplished by a system for the production of a medical product, above all a bag, composed of multiple plies of planar sections, particularly having film and/or nonwoven, having a semi-finished product transport system, particularly a tray transport system, having a main line and multiple feed lines disposed laterally, wherein semi-finished product feed units are provided in order to automatically feed pre-worked semi-finished products from the feed lines to the main line, having feed line tools on the feed lines, and having a main tool on the main line, wherein the feed lines and the main line have the same working height.

The term "working height" should be understood to mean the height at which the sections of the plies are guided in at least one tool of at least one feed line and main line, with reference to a horizontal working floor on which the system is set up.

To put it into simple words, the second aspect of the invention provides that as many as possible, but at least some work steps occur at the same working height.

In this manner, the semi-finished product feed unit does not have to be adjusted in height when two feed lines are interchanged, for example in the case of a product change. It is particularly advantageous if the feed lines have the same working height at the transfer station to the transfer device, in other words to the semi-finished product feed unit, as the height that the subsequent tool after the feed, in each instance, has in the main line.

The preferred embodiment of the system provides that all the tools of the main line, in any case to the extent that feed lines are still connected in this section, as well as the related end positions of the feed lines, in each instance, lie at the same working height, but above all, all of them do.

According to a third aspect of the present invention, the stated task is accomplished by a system for the production of a medical product, above all a bag, composed of multiple plies of planar sections, particularly having film and/or nonwoven, having a semi-finished product transport system, particularly a tray transport system, having a main line and multiple feed lines disposed laterally, wherein semi-finished product feed units are provided, in order to feed pre-worked semi-finished products from the feed lines to the main line, having feed line tools on the feed lines, and having a main tool on the main line, wherein the semi-finished product feed unit has a spreader device for the semi-finished product to be fed in.

The third aspect of the present invention provides, in simple words, that the transfer device, in other words the semi-finished product feed unit, spreads out the semi-finished product, in other words the section of the ply to be produced.

Spreading should take place at least temporarily.

Preferably, however, the semi-finished product is transferred to the main line in the spread-out state.

"Spreading" is understood to mean that the semi-finished product is elastically or plastically stretched in at least one of its two dimensions. The stretch is preferably fixed in place during transfer to the main line.

It is advantageous if the third aspect of the invention achieves the result that possible sagging sections or corrugations are tightened up, so that the main line can work independent of such imprecisions. The quality of the product is thereby improved.

It should be explicitly emphasized that two of the three invention aspects introduced above can also be used at the same time, in any desired combination, thereby causing synergy effects once again. All three of the aforementioned aspects can also be implemented at the same time.

Preferably, a main welding tool is provided on the main line.

A main welding tool is provided for the purpose of connecting the different semi-finished products with one another to form the ultimately multi-ply medical product, above all bag. Even before, partial connections can already be provided, either on the main line or also in the feed lines.

A feed line preferably has a pre-welding tool; above all, multiple feed lines can each have a pre-welding tool. Pre-welds can thereby take place even before transfer of the semi-finished products to the main line.

Alternatively or cumulatively, the feed line can have a pre-punching tool or multiple pre-punching tools or other severing tools.

Both the feed lines and the main line can furthermore have a combined welding/severing tool.

If the semi-finished product feed unit has grippers that can be moved apart from one another by a motor, it is particularly easy to spread the semi-finished product out in the feed to the main line.

Preferably, a controller is provided, in which the dimension of the spreading can be adjusted.

It is proposed that the semi-finished product feed unit has four grippers, above all precisely four grippers.

The sections of the plies, in other words the semi-finished products, will be very easy to handle, in practice, if they have an essentially rectangular shape. In the case of a plurality of grippers, it is therefore proposed that the grippers grip at a corner of the semi-finished product, in each instance, thereby in the case of an at least essentially rectangular semi-finished product, precise four grippers grip precise one corner of the semi-finished product, in each instance. The grippers can then undertake spreading of the semi-finished product in one or in two directions, in particularly simple manner.

If the semi-finished product feed unit has grippers in the form of needles, then the semi-finished product can be seamed in, in proven manner, by means of a simple insertion of the needle, preferably in the region of the corner. It is then particularly easy to transfer the semi-finished product to the main line in precise manner.

In order to maintain the spread-out state of the semi-finished product on the main line, it is proposed that the semi-finished product feed unit has deposition means for the semi-finished product in the tensed state, in order to place these on tension holders of the main line on the semi-finished product transport system.

"In the tensed state" should also be understood to mean a relaxed state that can occur after an original tensed state, for example when the plastic is still warm.

It has already been mentioned that preferably, all the semi-finished product feed units can be set up to grip and/or deposit at an identical height.

If the system is set up for guiding trays in the machine direction on precisely one plane, the transfer of the semi-finished products from the feed lines to the main line is also facilitated.

Furthermore, it is particularly easy to define a second plane in which the trays are returned, in order to result in a preferably endlessly circulating system.

Preferably, a waiting position can be provided between two semi-finished product feed units on the main line.

This possibility is particularly good if the transport means of the semi-finished product transport system are discrete, for example trays. In particular, the individual transport means should be individually controllable. This makes it possible to uncouple the working cycles of different feed lines and/or the main line from one another.

The semi-finished product feed units can preferably be disposed on the tray transport system in modular manner.

It is then conceivable to allow trays, each holding one or more semi-finished products, to be transferred from the semi-finished product feed unit to the main line, or to take the semi-finished products disposed on it from a tray that is only situated on the feed line, and to lay them down onto a tray that is situated only on the main line.

It is perceived to be advantageous if the semi-finished product feed unit has a defective part removal branch.

For this purpose, a sensor is preferably provided, above all an optical and/or mechanical sensor. A controller can then recognize whether a defective part is coming from the feed line. This part can be brought into a scrap collector from the semi-finished product feed unit—instead of being introduced into the main line. The semi-finished product feed unit is particularly suitable because it has a gripper device for the semi-finished products at the end of the feed line in any case.

The main line can have a linear transport direction. In the case of such a transport direction, the feed lines are preferably disposed at the same angle, particularly orthogonal to the machine direction of the main line.

Alternatively, different other transport directions are conceivable, for example oval transport directions, or a large indexing turret can be provided, which is indexed by an indexing angle and brings about transport during this process.

In order to produce a medical bag, it is conceivable, above all, that at least four plies, above all precisely four plies, are connected with one another for production of the product.

The semi-finished product transport system can be synchronized with the semi-finished product feed units.

According to a fourth aspect of the present invention, the stated task is accomplished by a method for operation of a system as described above.

This system is ideally operated to produce a medical product.

If a product change is supposed to be made during production, this can be brought about, in simple manner, in that one or more feed lines are interchanged.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings.

DETAILED DESCRIPTION OF PREFERRED EMBODIMENTS

Figure 1:
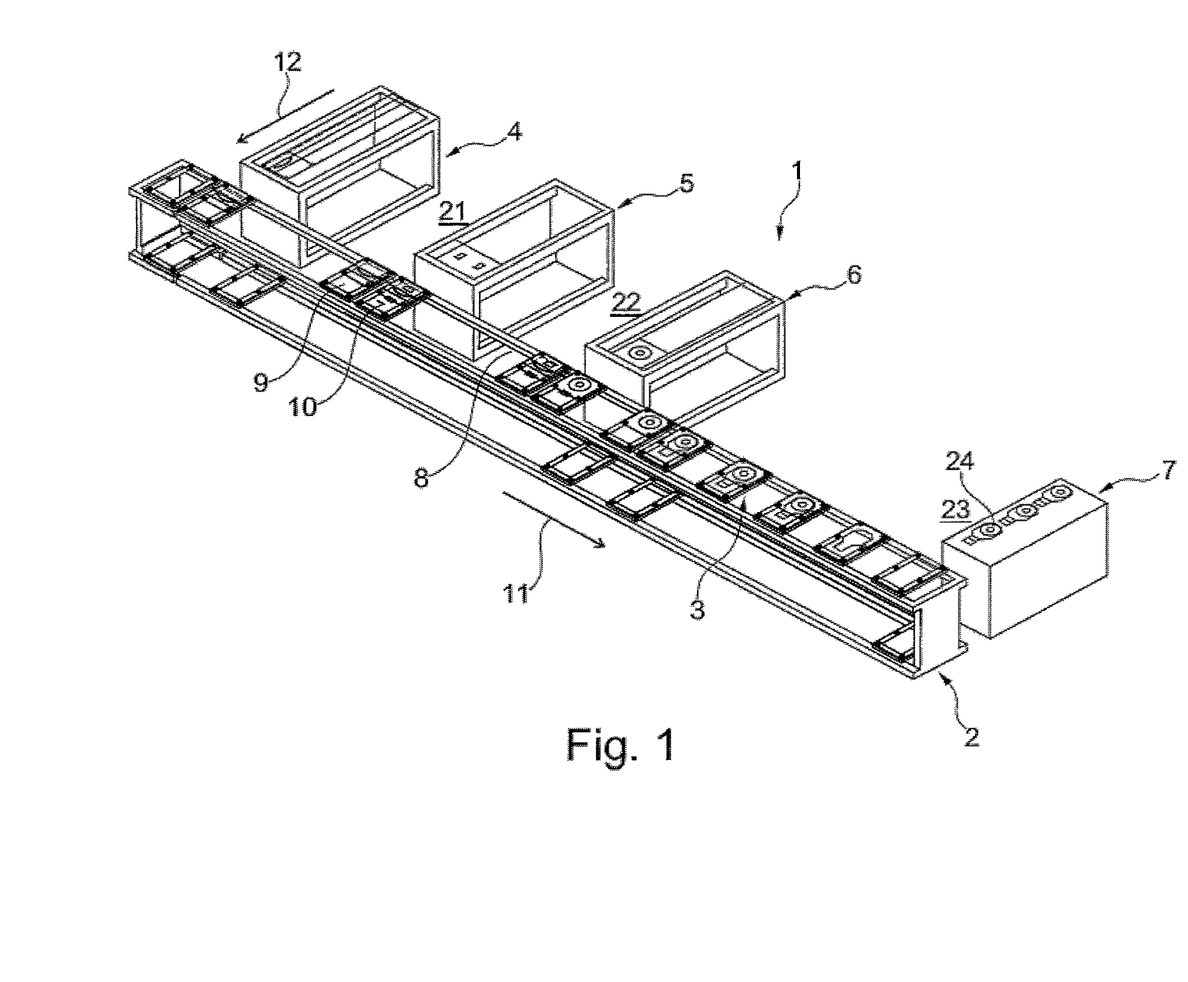
FIG. 1 shows schematically, in a perspective view, a system for the production of colostomy bags, having a main line, having three feed lines, and having a finished product line.

The system 1 in FIG. 1 is a system for the production of colostomy bags, set up in modular manner. It should be explicitly pointed out that the most varied different kinds of other multi-ply products can advantageously be produced in such a system, as well.

The system 1 consists essentially of a main line 2 having a tray transport system 3 as well as having a first feed line 4, a second feed line 5, and a third feed line 6, as well as having a finished part transfer unit 7 also configured as a lateral line.

The tray transport system 3 in the main line 2 consists of a linear guide 8, in which a plurality of trays 9 (numbered as examples) are guided so as to be driven in longitudinally displaceable manner and preferably individually.

Each tray 9 has a rectangular contact or supporting surface 10 for accommodating semi-finished products or finished products.

The trays 9 are set up for being transported in a machine direction 11.

In the concrete exemplary embodiment presented here, a plane that lies underneath guides the trays back again, counter to the machine direction 11, in an endless circuit in the main line 2.

To the side of the main line 2, the three feed lines 4, 5, 6 are standing at an orthogonal angle here, so that the main line 2 transports through the system 1 in the main machine direction 11, while the feed lines 4, 5, 6 feed semi-finished products to the main line in the feed machine directions 12 (shown as an example).

The feed lines 4, 5, 6 have tools for different pre-working processes.

The feed lines 4, 5, 6 and the main line 2 furthermore each have a working height, wherein the working heights are identical not only in the feed lines 4, 5, 6 but also in the main line.

From every feed line 4, 5, 6, there is a transfer device (not shown), which is set up for taking over semi-finished products being transported in a feed machine direction from the feed lines 4, 5, 6, and placing the trays 9 into the main line 2.

The tools are not shown here.

In a standard case, the main line 2 will have a main welding tool (also not shown), in any case.

Figure 2:
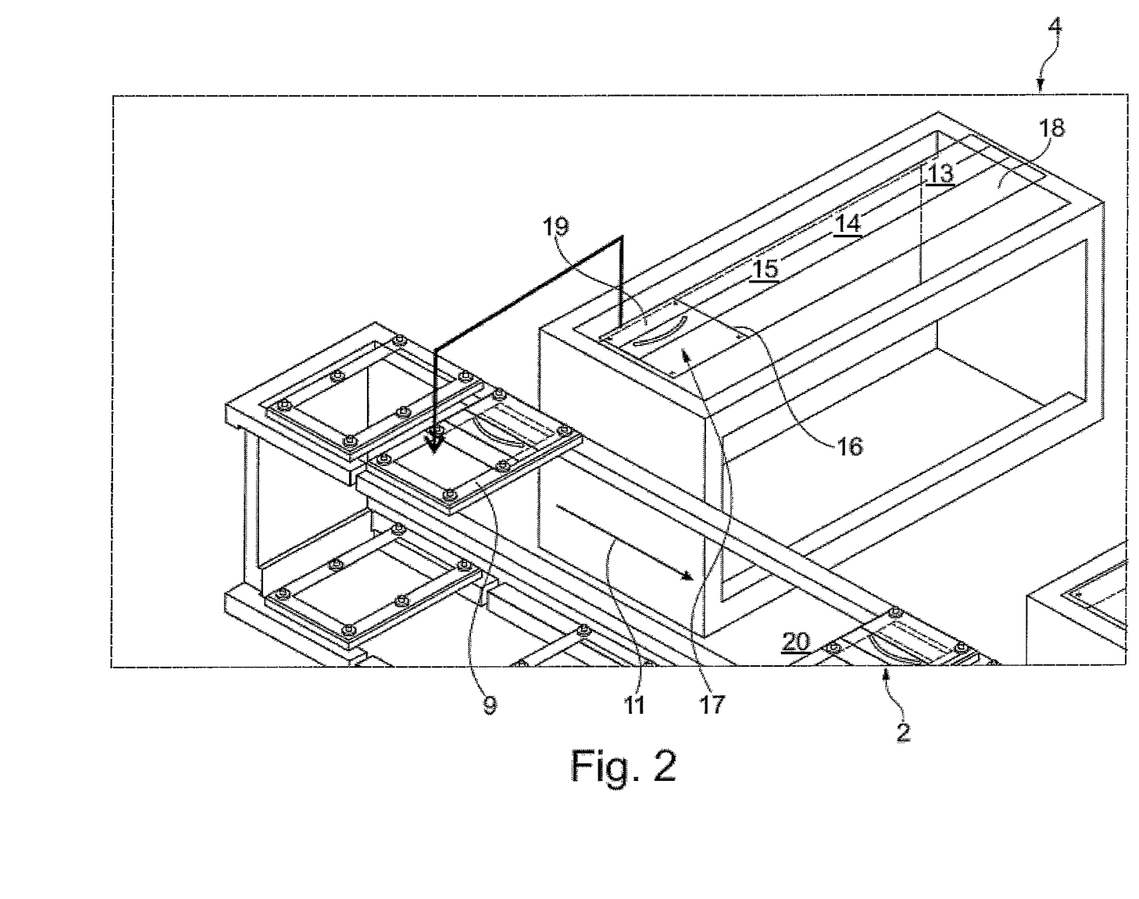
FIG. 2 shows schematically, in a detail view from FIG. 1, a possible first feed line.

The first feed line 4, or also every other feed line, can be structured as follows, for example (see FIG. 2):

First, unwinding of a film from a roll takes place at a first position 13.

In a subsequent position 14, pre-welding takes place.

In a further subsequent position 15, punching or cutting takes place.

A severing cut 16 can also take place at a station, combined or separately. The severing cut 16 separates a film section 17 from the incoming endless film band or strip 18.

Here, the film section 17 is left rectangular. The shape of the film section 17 fundamentally corresponds, in this regard, with that of the tray 9.

Four small holes 19 (numbered as an example) are punched into the film section 17, also already in the feed line 4, specifically precisely in the corners of the rectangular film section 17.

A semi-finished product feed unit (not shown) performs a transfer of the semi-finished products in the form of the now separated film sections 17 from the feed line 4 to the main line 2, in concrete terms by gripping the film section 17, raising the film section 17, moving the film section 17 forward, while rotating it by 90°, and placing the film section 17 down onto the tray 9. In an individual case, whether or not a film section 17 or another semi-finished product is rotated during the transfer will always depend on the shape of the incoming semi-finished products and the shape of the transport means.

Subsequently, the tray 9 can be transported further along the main line 2 in the machine direction 11.

At the same time, further semi-finished products can be pre-produced along the feed line 4 and transferred to further trays in the main line 2.

Because distances 20 are left between the individual trays 9 in the main line 2, the production cycle of the feed line 4 does not have to coincide with the advancing cycle in the main line 2.

Instead, it is also possible to provide for good part recognition or defective part removal before or during transfer from the feed line 4 to the main line 2.

The trays 9 can be used over their full area or over a partial area.

It should furthermore be explicitly pointed out that the exemplary embodiment shown here is a tray system. Other system geometries or types of transport, however, can also be provided; for example, the system can be structured as a turntable system or as an oval transport system.

Because only a single film plane exists, in other words the working heights of the incoming film web in the feed line, of the film sections, and of the trays are identical, the individual feed lines 4, 5, 6 can be set onto the main line 2 in modular manner, and therefore can also be interchanged with one another or replaced with other feed lines, not shown, for example in order to perform a product change.

The production accuracy is dramatically increased by these measures.

Furthermore, no tensile stresses of any kind on the film, which could come from a long film strip, are present in the main line 2, in other words in the line of the final processing steps such as, for example, the main welding process, because separation of the endless film strip 18 into film sections 17 already takes place earlier, namely in the feed lines 4, 5, 6.

Even in the case of a desired conversion of the system 1 for the production of a new product, this conversion is possible more easily than known in the state of the art: Conversion is easier because further modules serving as feed lines can be separately pre-assembled and then transported to the bag manufacturer by the machine manufacturer. Because of the uniform transfer interface from the feed lines 4, 5, 6 to the main line 2, such subsequently designed, modular feed lines can be retrofitted at any time.

In order to be able to refit the system 1 quickly, using existing modules, the modules can be moved in interstices 21, 22, for example, thereby parallel to the main line 2 and at a right angle to the feed machine direction 12.

Thus, for example, a linear mounting for the feed lines 4, 5, 6 on the main line 2 can be provided, in order to clearly fix the modular feed lines 4, 5, 6 in place at their distance from the main line 2.

At the end 23 of the main line 2, an extraction apparatus (not shown) for the finished products, here ostomy bags 24 (numbered as an example) is provided. The extraction device can preferably distinguish between good parts and defective parts and pass the defective parts to scrap, while the good parts of the ostomy bags 24 are laid down onto the finished part take-over unit 7 and can be transported further from there.

The second feed line 5 can particularly be configured in such a manner (see FIG. 3) that film unwinding at film unwinding unit 25 also takes place, at first, whereupon a filter is punched out and pre-welding is performed (position or station 26). Subsequently, a flap can be affixed (station 27). Finally, holes can be made in the corner region again, and a severing cut from the endless strip to an individual panel can take place (station 28). Subsequently, the transfer to a tray 29 standing ready can take place, wherein the tray 29 standing ready already carries a semi-finished product 30 from a previous feed line, here the first feed line 4.

Figure 3:
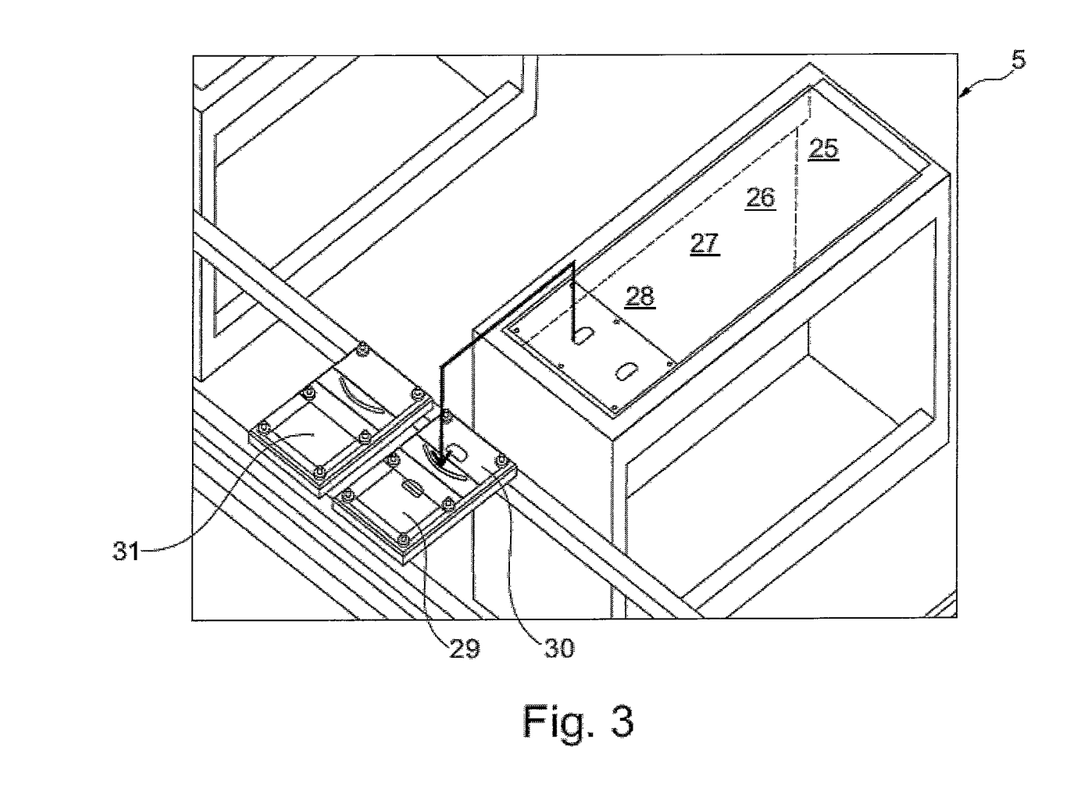
FIG. 3 shows schematically, in a detail view from FIG. 1, a possible second feed line.

By means of the holes in the corner region, which have already been introduced in the feed line, the different semi-finished products 30 being transferred from the feed lines 4, 5, 6 can be placed so that they are perfectly aligned, one on top of the other.

In the meantime, trays 31 situated in waiting position can stand still or perform individual movements, without slowing down the transfer at the second feed line 5 or the first feed line 4.

Figure 4:
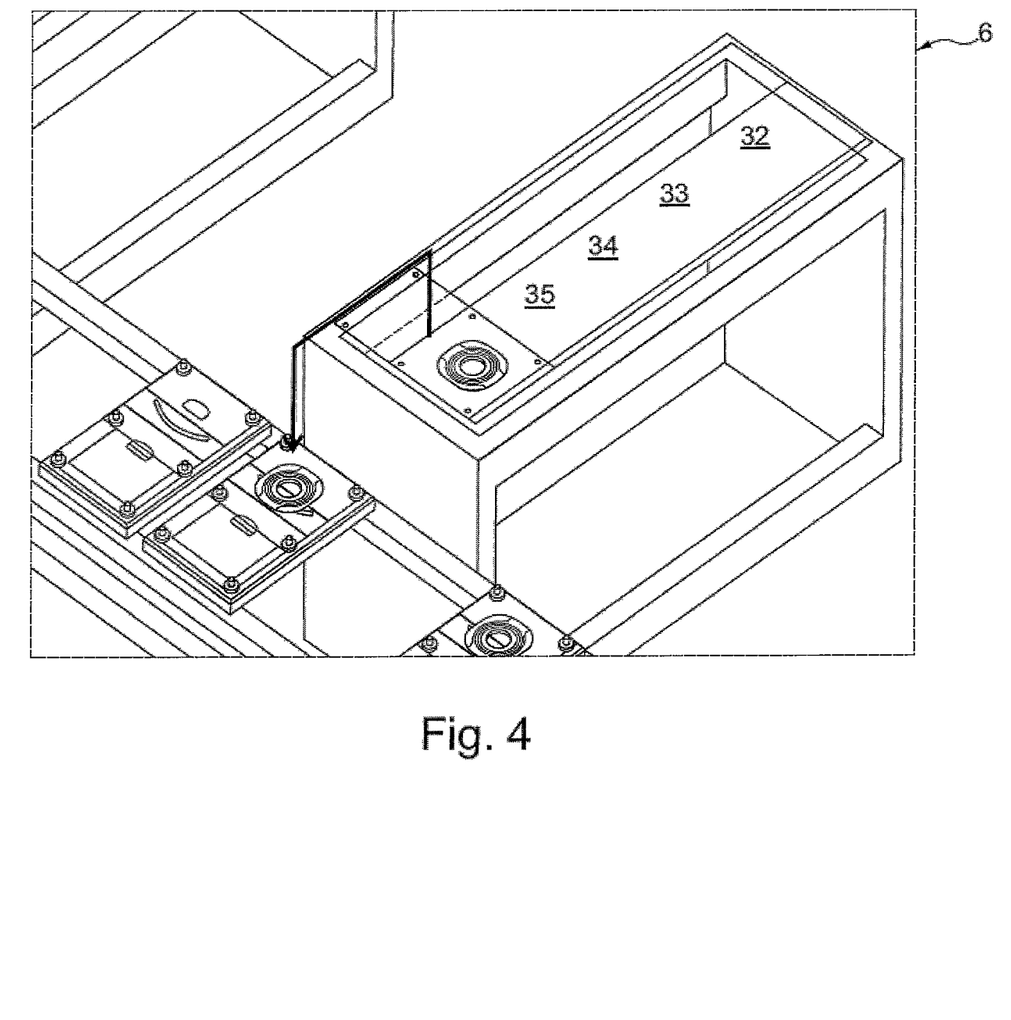
FIG. 4 shows schematically, in a detail view from FIG. 1, a possible third feed line.

A further feed line, here, for example, the third feed line 6, can be structured as follows (see FIG. 4):

Unwinding of a film strip (station 32) takes place first, once again. Subsequently, an inlet and/or outlet hole can be punched or taken out in some other manner (station 33). A flange can be fed in and welded on (station 34). Finally, a severing cut is preferably performed, once again, and centering and tensioning holes are introduced at the corners (station 35). The subsequent transfer once again positions the freshly supplied semi-finished product onto the semi-finished product that has already been transported to this location on the tray.

Figure 5:
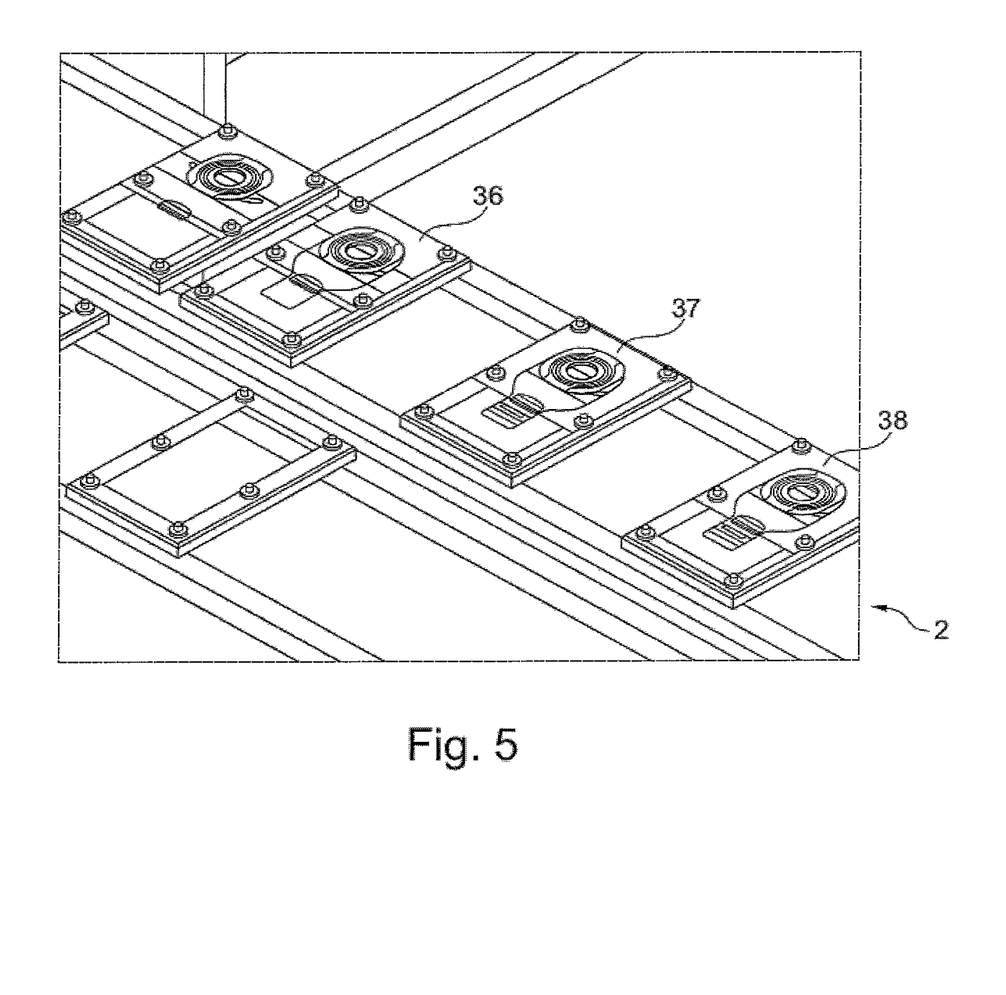
FIG. 5 shows schematically, in a detail view, the main line.

In the main line 2, further stations with processing tools can be provided ahead of the first feed line 4, after the last, here third feed line 6, as well as between the feed lines 4, 5, 6, for example a station 36 having a circumferential welding tool for the bag, a station 37 for affixing an identification label or for imprinting, as well as, for example, a further station 38 for quality control, for example by means of an optical inspection device (see FIG. 5).

At the end 23 of the main line, punching out then preferably takes place at a station 39, as does tearing out or other removal at a station 40, as well as finally, at an extraction unit 41 extraction of good parts as well as removal of defective parts.

Figure 6:
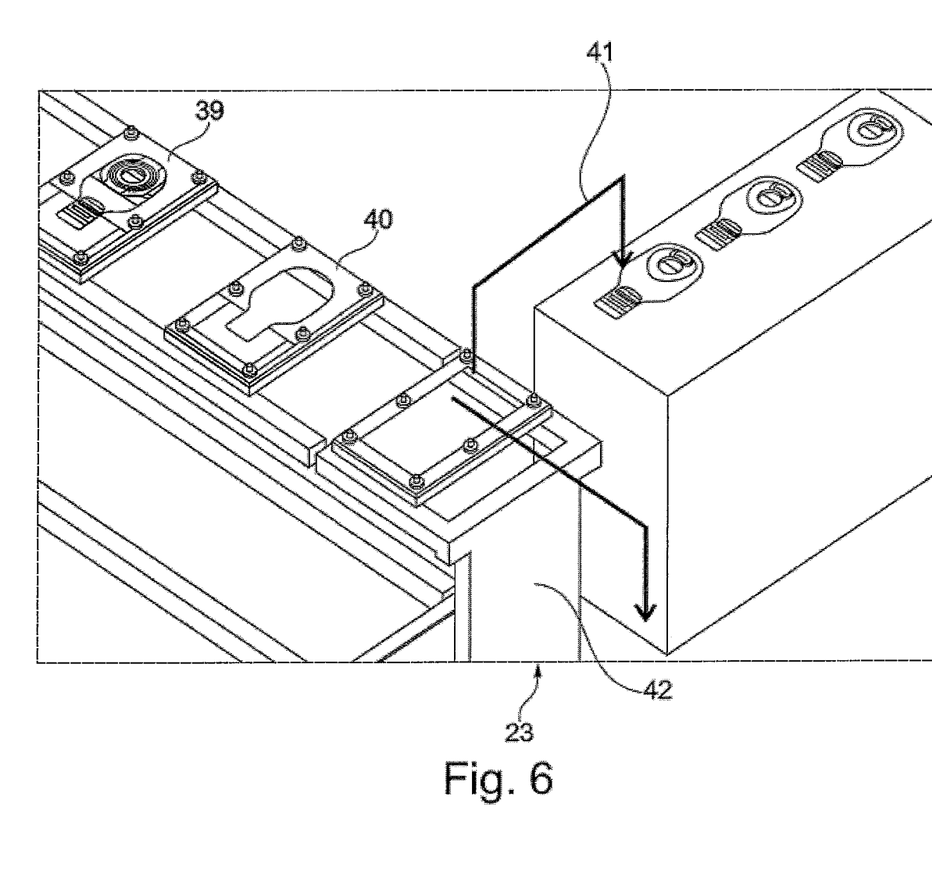
FIG. 6 shows schematically, in a detail from FIG. 1, an end of the main line, having a good part extraction unit and a good part table.

An elevator 42 serves for lowering the trays 9 from the working height of the main line 2 to a return transport height (see FIG. 6).

The semi-finished product feed unit (see FIGS. 7 to 9) has a complex gripper 43).

Figure 7:
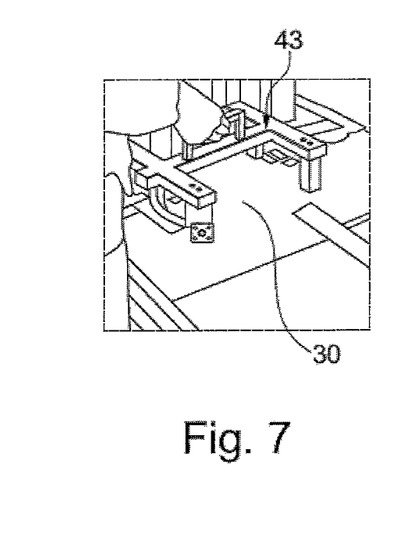
FIG. 7 shows in a perspective view, a transfer device from a feed line to the main line, with a grasped semi-finished product composed of film.
Figure 8:
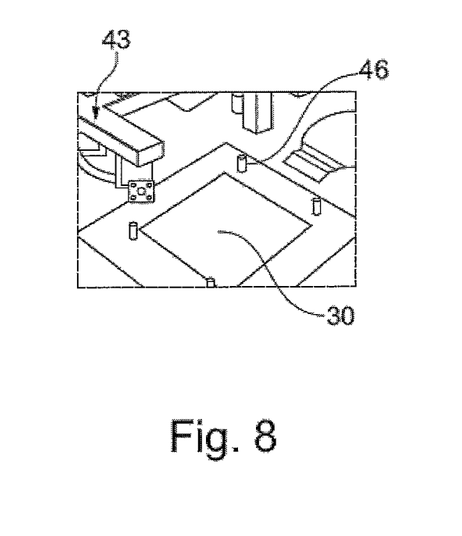
FIG. 8 shows the transfer device from FIG. 7 from a changed perspective.
Figure 9:
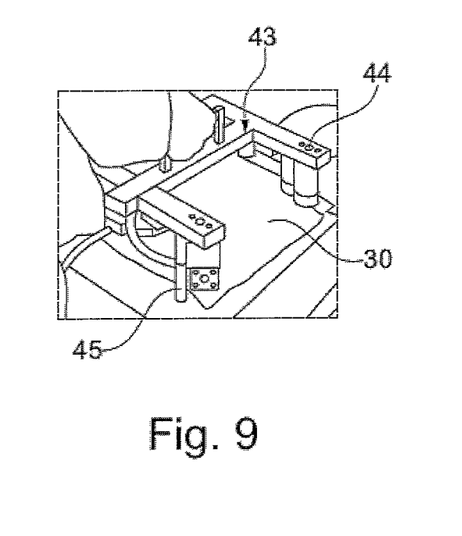
FIG. 9 shows the transfer device from FIGS. 7 and 8.

The gripper device 43 is mounted to float on the semi-finished product feed unit; it is centered by way of a sensor, wherein the sensor can be optical, for example, but can also be mechanical.

Alternatively, it is easy to imagine that the trays are mounted in floating manner.

It can also be imagined that the tray for laying the semi-finished product onto the tray is raised from its transport plane and centered.

The gripper device 43 has multiple grippers 44, 45 (numbered as an example), particularly precisely four grippers 44, 45.

The grippers 44, 45 are preferably adjusted on the gripper device 43 or moved forward in such a manner that they can grip the corners of the semi-finished product 30 to be gripped, particularly into the holes 19 provided there, or can align themselves relative to the holes 19, once again mechanically and/or optically, for example.

The grippers 44, 45 can preferably be adjusted electronically relative to one another, so that a tensile stress can be applied to the semi-finished product 30. This stress prevents semi-finished product 30 from sagging, wherein even already existing wrinkles can be smoothed out, so that the semi-finished product 30 can be laid onto centering pins 46 (numbered as an example) on the tray 29 that is standing ready, in the smoothest possible state.

Alternatively or cumulatively, it can be imagined that needle grippers are provided, which hold the cutouts in the main line 2.

It should be explicitly pointed out that the machine concept for the production of a multi-ply medical product already represents an invention, not necessarily restricted only to a production system for ostomy bags.

The production of ostomy bags is an advantageous embodiment of the invention.

A person skilled in the art will select all the other tools on the feed lines and the main line within the scope of designing a system for the production of a specific medical product, in a manner that appears suitable to him or her, for example with separate tools at separate stations, or with combined tools at combined stations, so that a combined welding/cutting tool can also be provided, for example, in place of individual stations for pre-welding or main welding and a station separate from them for cutting out or other separation.

In general, the invention presented here can be most advantageously used for medical products having multiple film plies and a main welding process as well as operations that precede a main welding process, wherein objects can also be affixed to the film, for example a flange or a flap.

In conventional systems, four film systems are generally guided in four planes, at a distance from one another, in order to allow tasks such as punching, filter pre-welding, etc. Only then are the films brought together in one plane and welded to one another.

In the case of product changes, however, the product switch is restricted with this concept, and every subsequent step is dependent on the preceding step.

In the new concept, the processing steps are divided up among the supplying modules, and finished pre-worked (for example pre-punched or pre-welded cutouts) are collected on the tray and only then finally welded.

A further special feature is the spreading possibility of the needle grippers, for example four grippers mounted in the corners. As a result, sagging is prevented, and possible wrinkles are smoothed out.

What is achieved is the production of a product composed of multiple plies of film and/or nonwoven and additional components.

Although only a few embodiments of the present invention have been shown and described, it is to be understood that many changes and modifications may be made thereunto without departing from the spirit and scope of the invention.

What is claimed is:

1. A system for production of an ostomy bag composed of a plurality of plies of at least one of a film and a nonwoven, the system comprising:

(a) a semi-finished product transport system having a main line and a plurality of lateral feed lines directly feeding the main line each with the help of a respective transfer device, wherein the plurality of the feed lines are different from each other by different feed line tools on the feed lines, and wherein some of the plurality of different lateral feed lines are placed between a first of the plurality of feed lines and a finish part transfer unit directly feeding from the main line;

(b) a plurality of semi-finished product feed lines for feeding pre-worked semi-finished products from the feed lines to the main line in an automated manner, wherein each of the feed lines has its own semi-finished product feed lines; and (c) a main line tool on the main line;

wherein the number of the transfer devices is identical to the number of lateral feed lines.

2. The system according to claim 1, wherein the ostomy bag is a colostomy bag and the semi-finished product transport system is a tray transport system.

3. A system for production of a medical product composed of a plurality of plies of planar sections, the system comprising:

(a) a semi-finished transport system having a main line and a plurality of lateral feed lines directly feeding the main line with the help of a transfer device;

(b) a plurality of semi-finished product feed units for automatically feeding pre-worked semi-finished products from the feed lines to the main line;

(c) a plurality to feed line tools on the feed lines; and (d) a main line tool on the main line;

wherein the feed lines and the main line have an identical working height so as to set the individual feed lines onto the main line in modular manner and so as to make the individual feed lines interchangeable with one another or so as to replace with other feed lines in order to perform a product change; and wherein the number of the transfer devices is identical to the number of lateral feed lines.

4. The system according to claim 3, wherein the medical product is a bag, the plurality of plies of planar sections comprise at least one of a film and a nonwoven and the semi-finished product transport system is a tray transport system.

5. A system for production of a medical product composed of a plurality of plies of planar sections, the system comprising:

(a) a semi-finished product transport system having a main line and a plurality of lateral feed lines directly feeding the main line with the help of a transfer device;

(b) a plurality of semi-finished product feed units for automatically feeding pre-worked semi-finished products from the feed lines to the main line, each semi-finished product feed unit having a spreading device configured to elastically or plastically stretch the semi-finished product in at least one dimension and configured to feed in the semi-finished product;

(c) a plurality of feed line tools on the feed lines; and (d) a main tool on the main line;

wherein the number of the transfer devices is identical to the number of lateral feed lines.

6. The system according to claim 5, wherein the medical product is a bag, the plurality of plies of planar sections have at least one of a film and a non-woven, and the semi-finished product transport system is a tray transport system.

7. The system according to claim 1, wherein the main line has a main welding tool.

8. The system according to claim 1, wherein one of the feed lines has a pre-welding tool.

9. The system according to claim 1, wherein one of the feed lines has a pre-punching tool.

10. The system according to claim 3, wherein each semi-finished product feed unit has grippers movable apart from one another by a motor.

11. The system according to claim 3, wherein one of the semi-finished product feed units has four grippers.

12. The system according to claim 3, wherein each semi-finished product feed unit has grippers provided to grip at corners of the semi-finished product.

13. The system according to claim 3, wherein each semi-finished product feed unit has grippers formed as needles.

14. The system according to claim 3, wherein each semi-finished product feed unit has a deposit device for the semi-finished product in a tensed state in order to place the semi-finished product on tension holders of the main line on the semi-finished product transport system.

15. The system according to claim 3, wherein all the semi-finished product feed units are set up for at least one of gripping and depositing at an identical height.

16. The system according to claim 1, wherein the system is set up for guiding trays in a machine direction on precisely one plane.

17. The system according to claim 3, wherein a waiting position is provided between two of the plurality of semi-finished product feed units.

18. The system according to claim 4, wherein the semi-finished product feed unit is disposed on the tray transport system in a modular manner.

19. The system according to claim 3, wherein the semi-finished product feed unit has a defective part removal branch.

20. The system according to claim 1, wherein the main line has a linear transport direction.

21. The system according to claim 3, wherein four plies are connected with one another to produce the medical product.

22. The system according to claim 3, wherein the semi-finished product transport system is synchronized with each semi-finished product feed unit.

23. A method for operation of the system of claim 1, claim 3, or claim 5 for production of a medical product, the method comprising:
   (a) providing the system comprising a semi-finished transport system having a main line and a plurality of lateral feed lines directly feeding the main line with the help of a transfer device, a plurality of semi-finished product feed units for automatically feeding pre-worked semi-finished products from the feed lines to the main line, a plurality of feed line tools on the feed lines, and a main line tool on the main line, wherein the feed lines and the main line have an identical working height; and
   (b) interchanging at least one feed line to undertake a change in product;
   wherein the number of the transfer devices is identical to the number of lateral feed lines.

\* \* \* \* \*